United States Patent [19]

Kimae et al.

[11] Patent Number: 5,750,753
[45] Date of Patent: May 12, 1998

[54] METHOD FOR MANUFACTURING ACRYLOXYPROPYSILANE

[75] Inventors: Yoichi Kimae; Shunji Yoshimatsu; Norio Itoda; Takashi Matsuo, all of Kumamoto; Naoki Noda, Chiba, all of Japan

[73] Assignee: Chisso Corporation, Osaka, Japan

[21] Appl. No.: 777,595

[22] Filed: Dec. 31, 1996

[30] Foreign Application Priority Data

Jan. 24, 1996 [JP] Japan ................... 8-031449

[51] Int. Cl.$^6$ ................................................... C07F 7/08
[52] U.S. Cl. ................................................... 556/440
[58] Field of Search ................................. 556/440

[56] References Cited

U.S. PATENT DOCUMENTS

| | | | |
|---|---|---|---|
| 3,658,866 | 4/1972 | Tsuji et al. | 556/479 |
| 3,864,372 | 2/1975 | Svoboda et al. | 556/440 X |
| 4,292,433 | 9/1981 | Koga et al. | 556/479 |
| 4,309,558 | 1/1982 | Koga et al. | 556/479 |
| 5,191,103 | 3/1993 | Mehta et al. | 556/479 |

FOREIGN PATENT DOCUMENTS

| | | |
|---|---|---|
| 50-24947 | 8/1975 | Japan. |
| 56-29873 | 7/1981 | Japan. |
| 59-213728 | 12/1984 | Japan. |
| 61-236786 | 10/1986 | Japan. |

*Primary Examiner*—Paul F. Shaver
*Attorney, Agent, or Firm*—Wenderoth, Lind & Ponack

[57] ABSTRACT

A method to manufacture acryloxypropylsilane to a high degree of purity is achieved by hydrosilation of (A) allyl acrylate or allyl methacrylate by (B) a hydrosilane compound, using (C) a platinum-containing compound as the catalyst and (D) an organic phosphorus compound as the promoter. The acryloxypropylsilane product is expressed by General Formula I $$CH_2=CR^1COOCH_2CH_2CH_2SiR^2{}_nR^3{}_{3-n} \quad \text{(Formula I)}$$

where $R^1$ represents a hydrogen or methyl group, $R^2$ represents a hydrolyzable group, $R^3$ represents an aryl, alkenyl or aryl group of carbon number 1–12, and n is 0, 1, 2, or 3.

2 Claims, No Drawings

METHOD FOR MANUFACTURING ACRYLOXYPROPYSILANE

BACKGROUND OF THE INVENTION

1. Field of Invention

This invention relates to a manufacturing method for silane, specifically acryloxypropyl and methacryloxypropyl derivatives of silane (hereinafter referred to as acryloxypropylsilane), and in particular, a manufacturing method that produces few by-products.

2. Description of the Prior Art

Acryloxypropylsilane has a wide range of applications, including use as a silane coupling agent, raw material for other silane coupling agents, raw material for polysiloxane, terminating agent in the manufacturing process of polysiloxane, surface treating agent for a variety of substrates and denaturant for various resins. In these applications, there is increasing demand for highly functional, value added products. Accordingly, an unprecedented high degree of purity is required for acryloxypropylsilane as a raw material for these applications.

Acryloxypropylsilane is conventionally manufactured in the following way: Allyl acrylate or allyl methacrylate and hydrosilane compounds are hydrosilated in the presence of platinum or other transition metal catalyst, and then the product solution is distilled under reduced or atmospheric pressure.

Hydrosilation in the presence of a transition metal catalyst shows high chemoselectivity and regioselectivity. In the hydrosilation of allyl acrylate, there are three reaction sites, that is, the C—C double bond of the allyl group, the C—C double bond of acrylate, and the C—O ester double bond of acrylate, but the reaction preferentially takes place at the allyl group because of chemoselectivity.

Furthermore, when there is hydrosilation at the allyl group, both beta and gamma adducts are potentially formed by the addition of silicon to the respective sites; however, the gamma adduct is the preferred product because of regioselectivity.

However, hydrosilation in the presence of a transition metal catalyst does not always show complete chemospecificity or regiospecificity. Hydrosilation of allyl acrylate or allyl methacrylate produces a gamma adduct, acryloxypropylsilane, by addition to the allyl group; this is the desired product. This reaction, however, produces other by-products: a beta adduct, a compound formed by addition to the C—C double bond of acrylate or methacrylate and a compound formed by addition to the C—O ester double bond. These by-products have boiling points close to that of the desired product, acryloxypropylsilane, and it is extremely difficult to separate the by-products from the desired product by distillation.

To manufacture acryloxypropylsilane to a high degree of purity, a synthesis method that shows high chemoselectivity and regioselectivity is necessary. In particular, a catalyst system that ensures chemoselectivity and regioselectivity in hydrosilation is necessary.

Previously reported methods to manufacture acryloxypropylsilane include:

In Japanese Patent Publication No. 24947/75, a beta diketone-platinum complex was used as the catalyst to produce a high-yield of the desired product with virtually no side reactions. The synthesis of 3-methacryloxypropylsilane was given as an example. Although it was mentioned that there is improved efficiency as compared with hexachloroplatinic acid, no reference was made as to how chemoselectivity and regioselectivity are improved.

In Japanese Patent Publication No. 29873/81, a reaction using phenothiazine, diphenylamine or N, N'-diphenyl-p-phenylendiamine as an accelerating agent in the presence of a platinum catalyst was introduced as a means to improve the regioselectivity of hydrosilation. However, no explanation was made as to how to synthesize acryloxypropylsilane. Also, no reference was made of chemoselectivity or regioselectivity with respect to allyl acrylate or allyl methacrylate.

Laid-open Japanese Patent Publication No. 213728/84 provides a synthesis model for 3-acryloxypropylmethyldichlorosilane, but no reference was made of chemoselectivity or regioselectivity with respect to allyl acrylate.

Laid-open Japanese Patent Publication No. 236786/86 introduced synthesis methods for 3-acryloxypropyltrichlorosilane and 3-methacryloxypropyltrichlorosilane. It was simply stated that a reaction is carried out with octyl alcohol solution of hexachloroplatinic acid as the catalyst. No details were given regarding chemoselectivity or regioselectivity.

Examples of 3-acryloxypropylethyldichlorosilane, 3-acryloxypropylmethyidichlorosilane, 3-acryloxypropyldimethylchlorosilane and 3-acryloxypropyltrichlorosilane syntheses are given in a paper by Efimov et al. (Zh.Obsch. Khim. (1991) 61 (10) 2244–53). A description of hydrosilation using hexachloroplatinic acid and phenothiazine was given, but no details were provided regarding chemoselectivity or regioselectivity.

The focus so far has been exclusively on the chemoselectivity and regioselectivity inherent in hydrosilation. No technical effort has been made to improve these selectivities. There has been even no recognition that it is important to exploit these selectivities to improve hydrosilation.

SUMMARY OF THE INVENTION

In light of the technical challenge to develop a method of hydrosilation which ensures a high level of chemoselectivity and regioselectivity in the manufacture of acryloxypropylsilane to a high degree of purity, the invention as claimed provides a reaction method that minimizes the formation of by-products which have boiling points close to that of the desired compound, acryloxypropylsilane.

The invention as claimed is a reaction method consisting of the following items 1 to 4:

1. A manufacturing method featuring the use of a platinum-containing compound as the catalyst and an organic phosphorus compound as the promoter in the process of manufacturing acryloxypropylsilane, expressed by General Formula (I), by Hydrosilation of allyl acrylate or allyl methacrylate with a hydrosilane compound.

$$CH_2=CR^1COOCH_2CH_2CH_2SiR^2{}_nR^3{}_{3-n} \qquad \text{(Formula I)}$$

$R^1$ represents a hydrogen or methyl group, $R^2$ represents a hydrolyzable group, $R^3$ represents an alkyl, alkenyl or aryl group of carbon number 1–12, and n is 0, 1, 2 or 3.

2. A manufacturing method as defined by Item 1 where the organic phosphorus compound is expressed by General Formula (II).

$$PR^4R^5R^6 \qquad \text{(Formula II)}$$

$R^4$, $R^5$ and $R^6$ represent an alkyl group of carbon number 1–10 or an aryl group of carbon number 6–10.

3. A manufacturing method as defined by Item 1 where the organic phosphorus compound is expressed by General Formula (III).

$$R^7R^8P(X)_mPR^9R^{10} \quad \text{(Formula III)}$$

$R^7$, $R^8$, $R^9$ and $R^{10}$ represent an alkyl group of carbon number 1–10 or an aryl group of carbon number 6–10. X represents $CH_2$ and m is 1,2, 3 or 4.

4. A manufacturing method featuring the mixture of allyl acrylate or allyl methacrylate and an organic phosphorus compound followed by the addition of a platinum-containing compound, and then the drop-fed addition of hydrosilane compound in the acryloxypropylsilane manufacturing method described in Item 1.

THE ADVANTAGE OFFERED BY THE INVENTION

This invention is a method to minimize the formation of by-products with boiling points close to that of the desired product, acryloxypropylsilane, which enables manufacture of the desired product to a high degree of purity. The product as manufactured in this manner has applications as a coupling agent and as a raw material for industrial use. This invention expands the applications of acryloxypropylsilane and has practical advantages.

DETAILED DESCRIPTION OF THE PREFERRED EMBODIMENTS

Details of the invention are described in this section.

This invention is a reaction method applied to the manufacture of acryloxypropylsilane. It involves an organic phosphorus compound which serves to minimize the formation of by-products that have boiling points close to that of the desired compound, acryloxypropylsilane.

Acryloxypropylsilane to which the invention relates is expressed by General Formula (I).

$$CH_2=CR^1COOCH_2CH_2CH_2SiR^2{}_nR^3{}_{3-n} \quad \text{(Formula I)}$$

$R^1$ represents a hydrogen or methyl group. $R^2$ represents a hydrolyzable group, such as chlorine, bromine or iodine, or an alkoxy or acetoxy group of carbon number 1–4. $R^3$ represents an alkyl, alkenyl or aryl group of carbon number 1–12, and n is 0, 1, 2 or 3.

Examples include:
3-Acryloxypropyltrichlorosilane
3-Acryloxypropylmethyldichlorosilane
3-Acryloxypropyldimethylchlorosilane
3-Acryloxypropylethyldichlorosilane
3-Acryloxypropyldiethylchlorosilane
3-Methacryloxypropyltrichlorosilane
3-Methacryloxypropylmethyldichlorosilane
3-Methacryloxypropyldimethylchlorosilane The reactants used in the invention are allyl acrylate or allyl methacrylate and a hydrosilane compound.

Hydrosilanes are compounds with at least one hydrogen atom bonded to a silicon atom.

Examples include:
Trichlorosilane
Methyldichlorosilane
Dimethylchlorosilane
Ethyldichlorosilane
Diethylchlorosilane
Phenyldichlorosilane
Diphenylchlorosilane The catalyst used in the invention is a platinum-containing compound. This includes inorganic compounds containing platinum, platinum complexes and catalysts where the carrier supports platinum. Hexachloroplatinic acid is one example. Platinum-containing compounds can be used either as is or dissolved or dispersed in a solvent that does not interfere with the reaction.

Although the quantity of the catalyst to be used is not specified, $10^{-9}$ to $10^{-3}$ gram-atom platinum per one mole allyl acrylate or allyl methacrylate is appropriate, with $10^{-8}$ to $10^{-6}$ gram-atom platinum being preferred.

The organic phosphorus compound used in the invention is expressed by General Formula (II) or (III).

$$PR^4R^5R^6 \quad \text{(Formula II)}$$

$R^4$, $R^5$ and $R^6$ represent an alkyl group of carbon number 1–10 or an aryl group of carbon number 6–10.

$$R^7R^8P(X)_mPR^9R^{10} \quad \text{(Formula III)}$$

$R^7$, $R^8$, $R^9$ and $R^{10}$ represent an alkyl group of carbon number 1–10 or an aryl group of carbon number 6–10. X represents $CH_2$, and m is 1, 2, 3 or 4.

Examples of organic phosphorus compounds include:
Triethylphosphine
Tri-n-propylphosphine
Tri-n-butylphosphine
Tri-sec-butylphosphine
Tri-tert-butylphosphine
Triisobutylphosphine
Tricyclohexylphosphine
Tri-n-hexylphosphine
Tri-n-octylphosphine
Triphenylphosphine
Tri-o-toluylphosphine
Tri-m-toluylphosphine
Tri-p-toluylphosphine
1,2-bis-(diphenylphosphino)ethane
1,3-bis-(diphenylphosphino)propane Of these compounds, triphenylphosphine, trihexylphosphine, 1,2-bis-(diphenylphosphino)ethane and 1,3-bis-(diphenylphosphino)propane are desirable for the invention, with triphenylphosphine being especially preferred.

The organic phosphorus compound can be used either as is or dissolved or dispersed in a solvent that does not interfere with the reaction.

The quantity of organic phosphorus compound to be used is preferably in the range of 0.1–50 moles per one gram platinum, with 1–10 moles being preferred.

Although the temperature for carrying out the reaction is not specified, it should generally be in the range of room temperature to 200° C., and more preferably in the range of 50°–120° C.

It is necessary to use polymerization inhibitors to inhibit the polymerization of unsaturated compounds during the reaction process. An inert gas containing oxygen may be used in combination with such an inhibitor at the discretion of the persons using the invention.

The embodiment of the invention is not limited to a particular reaction method. The application of reaction method can be determined at the discretion of the persons who make use of the invention. Examples include:

(1) A method to add the platinum-containing compound and organic phosphorus compound to the mixture of allyl acrylate or allyl methacrylate and hydrosilane compound;

(2) A method to add drop-fed hydrosilane compounds to the mixture of allyl acrylate or allyl methacrylate, platinum-containing compound and organic phosphorus compound;

(3) A method to add drop-fed allyl acrylate or allyl methacrylate to the mixture of hydrosilane compound, platinum-containing compound and organic phosphorus compound;

(4) A method to add drop-fed allyl acrylate or allyl methacrylate and hydrosilane compound simultaneously to the mixture of platinum-containing compound, organic phosphorus compound and solvent; or (5) Allyl acrylate or allyl methacrylate is first mixed with the organic phosphorus compound, to which the platinum-containing compound is added, followed by the drop-fed addition of the hydrosilane compound.

Of these methods, method (5) is the most preferable.

The role of the organic phosphorous compound in the reaction is not clearly understood at present. However, a paper by J. Gulinski et al. (Appl. Organomet. Chem., Vol. 8, 409–414 (1994)) contains a description that suggests a role for the organic phosphorus compound.

The paper reports that when hexachloroplatinic acid-cyclohexanone is used as the catalyst, due to the strong acidity of hexachloroplatinic acid, an aldol-condensed cyclohexanone compound is formed, which in turn forms stable platinum complexes. According to the paper, these complexes differ from the platinum colloids formed by the reduction of hexachloroplatinic acid by hydrosilane and show a high degree of reactivity and regioselectivity in hydrosilation. It is presumed that the organic phosphorus compounds used in the invention play a role similar to that of the aldol-condensed cyclohexanone compound described in the above paper. This probably results in better catalytic efficiency with a high degree of reactivity as well as strong regioselectivity and chemoselectivity. Therefore, it is important to introduce the platinum-containing compound and the organic phosphorus compound separately into the reactor. Moreover, it should be noted that effective catalysts are also formed in the reaction system due to the action of the hydrosilane compound.

The following is a detailed description of the invention with embodiments and reference examples shown. However, these embodiments do not set limits on the invention in any way.

The following conditions are employed for GC analysis in the embodiments and reference examples.

Glass column (length 3 meters and diameter 3 millimeters)

Column packing: liquid phase SE-30, 20%

Support: Shimalite WAW, 60/80 mesh

Carrier gas: helium

Flow rate: 60 ml/min

Detector: TCD

TCD temperature: 250° C.

Sample injection port temperature: 200° C.

Column initial temperature: 70° C.

Column final temperature: 250° C.

Step rate of temperature: 10° C./min.

EMBODIMENT 1

70.4 grams (0.628 moles) allyl acrylate, 2.1 grams BHT (2,6-ditertiallybutyl-4-methylphenol) as the polymerization inhibitor and 0.17 ml($5.72 \times 10^{-5}$ moles) 10% triphenylphosphine in toluene were mixed and heated to 90° C. Next, 0.15 ml 10% hexachloroplatinic acid ($5.0 \times 10^{-6}$ gram-atom platinum) in isopropanol was added to the mixture, and then 91 ml (0.826 moles) dimethylchlorosilane was drop-fed over a period of seven hours with the reaction temperature adjusted to between 90° and 100° C. 143.9 grams product solution was obtained upon completion of this process. GC analysis of the product solution showed that the desired product 3-acryloxypropyldimethylchlorosilane accounted for 46.2%. Two by-products of yields of 2.7% and 3.8% were also observed.

933.7 grams of the product solution obtained in Embodiment 1 was fractionally distilled by means of simple distillation. As a result, a 445.0 gram distillate of colorless and transparent liquid was obtained at 56°–58° C./1 mmHg. GC analysis of the distillate showed that 3-acryloxypropyldimethylchlorosilane accounted for 83% of the total volume of product solution.

$^1$H-NMR, $^{13}$C-NMR, and infrared absorption spectra and GC-MS profile of the distillate were measured, and the following data were obtained.

$^1$H-NMR (90 MHz): solvent CDCl$_3$

δ(ppm): 6.33 (1H, d, J=2.7 Hz), 6.18(1H, d, J=9.7 Hz), 5.80 (2H, dd, J=9.6 Hz, 2.7 Hz), 4.13 (2H, t, J=6.8 Hz), 1.95–1.60 (2H, m), 0.95 –0.70 (2H, m), 0.41 (6H, s)

$^{13}$C-NMR (22.5 MHz): solvent CDCl$_3$

δ(ppm): 165.4, 130.0, 128.4, 65.8, 22.2, 14.8, 1.2

Infrared absorption spectrum (cm$^{-1}$): 2950, 1725, 1635, 1255

GC-MS (EI, m/z): 27($C_2H_3^+$), 55($C_3H_3O^+$), 93($Me_2SiCl^+$)

GC-MS (CI, m/z): 93, 129(M—$C_3H_6$—Cl)$^+$, 135(M—$C_3H_3O_2$)$^+$, 165(M—$C_3H_5$)$^+$, 171(M—Cl)$^+$, 207(M+H)$^+$

These data show that the product obtained was 3-acryloxypropyldimethylchlorosilane, as expressed by Chemical Formula 1.

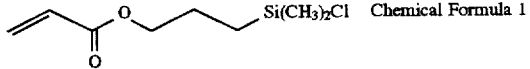

Chemical Formula 1

A colorless and transparent distillate was obtained at 35° C./3 mmHg as a result of the fractional distillation of the by-products formed in Embodiment 1. $^1$H-NMR, $^{13}$C-NMR, and infrared absorption spectra and GC-MS profile of the distillate were measured, and the following data were obtained.

$^1$H-NMR (90 MHz): solvent CDCl$_3$

δ(ppm): 5.96–4.93 (3H, m), 2.65–2.07 (3H, m), 1.13 (3H, d, J=6.6 Hz), 0.61 (6H, s), $^{13}$C-NMR (22.5 MHz): solvent CDCl$_3$ δ(ppm): 174.9, 135.0, 116.9, 40.3, 37.5, 16.1, 2.4

Infrared absorption spectrum (cm$^{-1}$): 3070, 1730, 1640, 1455, 1255, 1180, 920

GC-MS (EI, m/z): 27($C_2H_3^+$), 41($C_3H_5^+$), 68($C_5H_8^+$), 93($Me_2SiCl^+$), 137(M—$C_5H_9$)$^+$, 171(M—Cl)$^+$, 191(M—CH$_3$)$^+$

GC-MS (CI, m/z): 93, 115(M—Me$_2$SiCl+2H)$^+$, 171, 207 (M+H)$^+$

These data show that the product obtained was 2-methyl-4-pentenoxydimethylchlorosilane, as expressed by Chemical Formula 2.

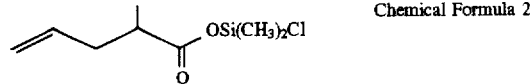

Chemical Formula 2

2-methyl-4-pentenoxydimethylchlorosilane, as expressed by Chemical Formula 3, is presumed to be the compound formed by a 1, 4 addition reaction followed by a Claisen rearrangement. This product is a result of poor chemoselectivity in hydrosilation.

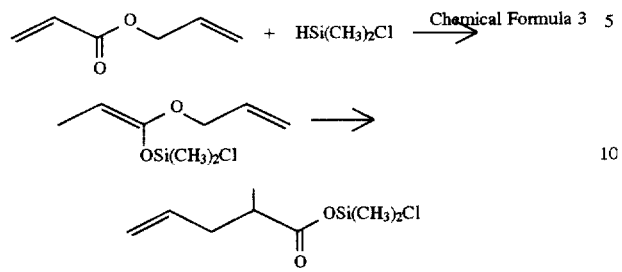

A colorless and transparent distillate was obtained by the fractional distillation at 28° C./1 mmHg of the by-products formed in Embodiment 1. $^1$H-NMR, $^{13}$C-NMR, infrared absorption spectra and GC-MS profile of the distillate were measured, and the following data were obtained.
$^1$H-NMR (90 MHz): solvent $CDCl_3$
δ(ppm):6.11–4.95 (3H, m), 4.55 (2H, d, J=5.8 Hz), 2.31 ($^1$H, q, J=7.2 Hz), 1.27(3H, d, J=7.1 Hz), 0.47(3H, s), 0.45(3H, s);
$^{13}$C-NMR (22.5 MHz): solvent $CDCl_3$
δ(ppm): 173.0, 132.2, 117.9, 64.8, 32.0, 10.4, 0.7, –0.2;
GC-MS (EI, m/z): 27($C_2H_3^+$), 41($C_3H_5^+$), 56($C_3H_5O$—H)$^+$, 93($Me_2SiCl^+$), 115(M—$Me_2SiCl$+2H)$^+$, 130(M—Cl—$C_3H_5$)$^+$, 149(M—$C_3H_5O$)$^+$
GC-MS (Cl, m/z): 93, 115, 131,149, 171(M—Cl)$^+$, 207(M+H)$^+$ These data show that the product obtained was 1-(allyloxycarbonyl) ethyldimethylchlorosilane, as expressed by Chemical Formula 4.

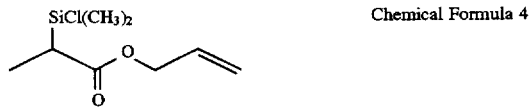

Chemical Formula 4

EMBODIMENT 2

A reaction was carried out in the same manner as Embodiment 1, except that 20 microliters (5.72×10$^{-5}$ moles) tri(n-hexyl)phospine was used instead of triphenylphosphine. As a result, 141.9 grams product solution was obtained. GC analysis showed that the desired product 3-acryloxypropyldimethylchlorosilane accounted for 45.6% of the total volume of product solution.

EMBODIMENT 3

A reaction was carried out in the same manner as Embodiment 1, except that 11.6 mg (2.86×10$^{-5}$ moles) of 1,2-bis(diphenylphospino)ethane was used instead of triphenylphosphine. As a result, 144.9 grams of product solution was obtained. GC analysis showed that the desired product 3-acryloxypropyldimethylchlorosilane accounted for 43.9% of the total volume of product solution.

EMBODIMENT 4

A reaction was carried out in the same manner as Embodiment 1, except that 12.2 mg (2.86×10$^{-5}$ moles) of 1,3-bis(diphenylphospino)propane was used instead of triphenylphosphine. As a result, 145.2 grams product solution was obtained. GC analysis showed that the desired product 3-acryloxypropyldimethylchlorosilane accounted for 34.8% of the total volume of product solution.

REFERENCE EXAMPLE 1

A reaction was carried out in the same manner as Embodiment 1, except that triphenylphosphine was not used. As a result, 151.0 grams of product solution was obtained. GC analysis showed that the desired product 3-acryloxypropyldimethylchlorosilane accounted for 18.8% of the total volume of product solution.

REFERENCE EXAMPLE 2

A reaction was carried out in the same manner as Embodiment 1, except that 14.9 microliters (5.72×10$^{-5}$ moles) of triphenylphosphite was used instead of triphenylphosphine. The reaction did not proceed further.

REFERENCE EXAMPLE 3

A reaction was carried out in the same manner as Embodiment 1, except that 8.0 microliters (5.72×10$^{-5}$ moles) triethylamine was used instead of triphenylphosphine. As a result, 145.5 grams product solution was obtained. GC analysis showed that the desired product 3-acryloxypropyldimethylchlorosilane accounted for 26.0% of the total volume of product solution.

REFERENCE EXAMPLE 4

A reaction was carried out in the same manner as Embodiment 1, except that 14.0 mg (5.72×10$^{-5}$ moles) triphenylamine was used instead of triphenylphosphine. As a result, 145.9 grams product solution was obtained. GC analysis showed that the desired product 3-acryloxypropyldimethylchlorosilane accounted for 21.6% of the total volume of product solution.

Table 1 shows the GC analytical values for the product solution obtained in embodiments 1–4 and Reference Examples 1–4. In the table, the desired product (1) is 3-acryloxypropyldimethylchlorosilane, and by-products (1) and (2) are 2-methyl-4-pentenoxydimethylchlorosilane and 1-(allyloxycarbonyl)ethyldimethylchlorosilane.

TABLE 1

Selectivity of the reaction using allyl acrylate and dimethylchlorosilane

| | Promoter | Desired Product(1) | By-Product(1) | By-product(2) |
|---|---|---|---|---|
| Embodiment 1 | PPh$_3$ | 46.2 | 2.7 | 3.8 |
| Embodiment 2 | P(n-hex)$_3$ | 45.6 | 2.8 | 4.1 |
| Embodiment 3 | Ph$_2$P(CH$_2$)$_2$PPh$_2$ | 43.9 | 3.6 | 3.7 |
| Embodiment 4 | Ph$_2$P(CH$_2$)$_3$PPh$_2$ | 34.8 | 6.6 | 3.7 |
| Reference Example 1 | — | 18.8 | 21.0 | 6.0 |
| Reference Example 2 | P(OPh)$_3$ | — | — | — |
| Reference Example 3 | NEt$_3$ | 26.0 | 17.2 | 5.0 |
| Reference Example 4 | NPh$_3$ | 21.6 | 19.4 | 6.0 |

EMBODIMENT 5

A reaction was carried out in the same manner as Embodiment 1, except that the reaction temperature was 60°–70° C. instead of 90°–100° C. GC analysis of the product solution showed that 3-acryloxypropyldimethylchlorosilane accounted for 51.4%, 2-methyl-4-pentenoxydimethylchlorosilane accounted for 1.7% and 1-(allyloxycarbonyl) ethyldimethylchlorosilane accounted for 2.5% of the total volume of product solution.

EMBODIMENT 6

A reaction was carried out in the same manner as Embodiment 1, except that the reaction temperature was 60°–70° C. instead of 90°–100° C. and 0.34 ml (11.44×10$^{-5}$ moles) instead of 0.17 ml (5.72×10$^{-5}$ moles) 10% triphenylphosphine in toluene was used. GC analysis of the product solution showed that 3-acryloxypropyldimethylchloro silane accounted for 47.7%, 2-methyl-4-pentenoxydimethylchlorosilane accounted for 2.2% and 1-(allyloxycarbonyl)ethyldimethylchlorosilane accounted for 3.7% of the total volume of product solution.

REFERENCE EXAMPLE 5

A reaction was carried out in the same manner as Embodiment 1, except that the reaction temperature was 60°–70° C. instead of 90°–100° C. and triphenylphosphine was not used. GC analysis of the product solution upon completion of the drop-fed addition of dimethylchlorosilane showed that a large quantity of dimethylchlorosilane was unreacted. The product solution was then aged for seventeen hours at 60°–70° C.

GC analysis of the product solution revealed that 3-acryloxypropyldimethylchlorosilane accounted for 31.2%, 2-methyl-4-pentenoxydimethylchlorosilane accounted for 9.2% and 1-(allyloxycarbonyl)ethyldimethylchlorosilane accounted for 4.4% of the total volume of product solution.

EMBODIMENT 7

A reaction was carried out in the same manner as Embodiment 1, except for the drop-fed addition of 69 ml (0.754 moles) methyldichlorosilane instead of dimethylchlorosilane. As a result, 153.4 grams product solution was obtained. GC analysis of the product solution showed the three products. The desired product 3-acryloxypropylmethyldichlorosilane accounted for 79.9% of the total volume of product solution.

A colorless and transparent distillate was obtained by fractional distillation at 59°–60° C./1 mmHg of the product solution obtained in Embodiment 7. The $^{13}$C-NMR spectrum and GC-MS profile of the distillate were measured, and the following data were obtained:

$^{13}$C-NMR(22.5 MHz): solvent CDCl$_3$
δ(ppm): 165.4, 130.2, 128.4, 65.2, 21.9, 17.8, 5.1
GC-MS (EI, m/z): 27(C$_2$H$_3$$^+$), 55(C$_3$H$_3$O$^+$),113(Me$_2$SiCl2$^+$), 154(M-C$_3$H$_3$O$_2$—H)$^+$
GC-MS (Cl, m/z): 73(C$_3$H$_3$O$_2$+2H)$^+$, 113, 137(M—Cl—C$_3$H$_3$O+H)$^+$, 155(M—C$_3$H$_3$O$_2$)$^+$, 227(M+H)$^+$ These data show that the product obtained was 3-acryloxypropylmethyldichlorosilane as expressed by Chemical Formula 5.

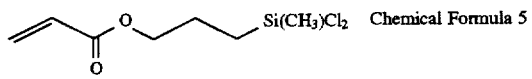

Chemical Formula 5

A colorless and transparent distillate was obtained by fractional distillation at 26° C./1 mmHg of the product solution obtained in Embodiment 7. The $^{13}$C-NMR spectrum and GC-MS profile were measured, and the following data were obtained:

$^{13}$C-NMR(22.5 MHz): solvent CDCl$_3$
δ(ppm): 173.0, 134.5, 117.2, 40.2, 37.2, 15.8
GC-MS (EI, m/z): 41(C$_3$H$_5$$^+$), 69(M—COOH)$^+$, 99(M—CH$_3$)$^+$, 114(M$^+$)
GC-MS (Cl, m/z): 97(M—OH)$^+$, 115(M+H)$^+$ These data show that the product obtained was 2-methyl-4-pentene acid as expressed by Chemical Formula 6.

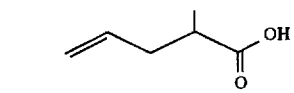

Chemical Formula 6

Regarding the by-products formed in Embodiment 7, the GC-MS profile was measured of the by-product that could not be separated by distillation of the product solution in Embodiment 7. As a result, the following data were obtained:

GC-MS (EI, m/z):27(C$_2$H$_3$$^+$), 41(C$_3$H$_5$$^+$), 113(Me$_2$SiCl$_2$$^+$), 141(M—C$_4$H$_5$O$_2$)$^+$, 169(M—C$_3$H$_5$O)$^+$
GC-MS (Cl, m/z):151(M—Cl—C$_3$H$_4$)$^+$, 193(M—Cl+2H)$^+$, 227(M+H)$^+$

These data show that the product obtained was 1-(allyloxycarbonyl)ethylmethyldichlorosilane as expressed by Chemical Formula 7.

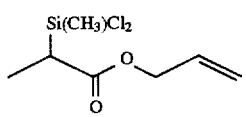

Chemical Formula 7

REFERENCE EXAMPLE 6

A reaction was carried out in the same manner as Embodiment 7, except that triphenylphosphine was not used. As a result, 155.9 grams product solution was obtained. GC analysis of the product solution showed that the desired product 3-acryloxypropylmethyidichlorosilane accounted for 45.3% of the total volume of the product solution.

Table 2 shows the GC values for the product solution obtained in Embodiment 7 and Reference Example 6. In the table, the desired product (2) is 3-acryloxypropylmethyldichlorosilane, and by-products (3) and (4) are 2-methyl-4-pentene acid and 1-(allyloxycarbonyl)ethylmethyldichlorosilane, respectively.

TABLE 2

Selectivity in the reaction using allyl acrylate and methyldichlorosilane

| | Promoter | Desired Product(2) | By-product(3) | By-product(4) |
|---|---|---|---|---|
| Embodiment 7 | PPh$_3$ | 79.7 | 0.1 | 0.4 |
| Reference Example 6 | — | 45.3 | 3.4 | 1.6 |

EMBODIMENT 8

A reaction was carried out in the same manner as Embodiment 1, except for the drop-fed addition of 76 ml (0.689 moles) trichlorosilane instead of dimethylchlorosilane. As a result, 160.9 grams product solution was obtained. GC analysis of the product solution showed that 3-acryloxypropyltrichlorosilane accounted for 83.6% of the total volume of product solution.

A colorless and transparent distillate with a boiling point of 67°–70° C./1 mmHg was obtained by simple distillation of the product solution. The GC-MS profile of the distillate was measured and the following data were obtained:

GC-MS (EI, m/z): 27(C$_2$H$_3$$^+$), 55(C$_3$H$_3$O$^+$), 133(SiCl$_3$$^+$), 174(M—C$_3$H$_3$O$_2$—H)$^+$
GC-MS (Cl, m/z): 73(C$_3$H$_3$O$_2$+2H)+, 133,175(M—C$_3$H$_3$O$_2$)$^+$, 211(M—Cl)$^+$, 227(M+H)$^+$

These data show that the product obtained was 3-acryloxypropyltrichlorosilane as expressed by Chemical Formula 8.

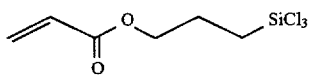 Chemical Formula 8

REFERENCE EXAMPLE 7

A reaction was carried out in the same manner as Embodiment 8, except that triphenylphosphine was not used. As a result, 162.5 grams product solution was obtained. GC analysis of the product solution showed that 3-acryloxypropyltrichlorosilane accounted for 70.7% of the total volume of product solution.

Regarding the by-products formed in Embodiment 7, the GC-MS profile was measured of the by-product that could not be separated by distillation of the product solution in Embodiment 7, and the following data were obtained:

GC-MS (EI, m/z):27($C_2H_3^+$), 41($C_3H_5^+$), 133($SiCl3^+$), 161 (M—$C^1H_5O_2$)$^{30}$, 189(M—$C_3H_5O$)$^+$
GC-MS (CI, m/z): 176(M—2Cl)$^+$, 211(M—Cl)$^+$, 247(M+H)$^+$

These data show that the product obtained was 1-(allyloxycarbonyl)ethyltrichlorosilane as expressed by Chemical Formula 9.

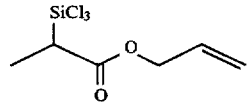 Chemical Formula 9

Table 3 shows the GC values for the product solution obtained in Embodiment 8 and Reference Example 7. In the table, the desired product (3) is 3-acryloxypropyltrichlorosilane, and the by-product (5) is 1-(allyloxycarbonyl)ethyltrichlorosilane.

TABLE 3

| Selectivity in the reaction using allyl acrylate and trichlorosilane | | | |
|---|---|---|---|
| | Promoter | Desired Product(3) | By-product(5) |
| Embodiment 8 | PPh$_3$ | 83.6 | — |
| Reference Example 7 | — | 70.7 | 0.4 |

What is claimed is:

1. A process of manufacturing acryloxypropylsilane expressed by Formula (I), $CH_2$=$CR^1COOCH_2CH_2CH_2SiR^2{}_nR^3{}_{3-n}$ (Formula I)

wherein $R^1$ represents hydrogen or methyl, $R^2$ represents a hydrolyzable group, $R^3$ represents an alkyl, alkenyl or aryl group of carbon number 1–12, and n is 0, 1, 2 or 3, which process comprises hydrosilating allyl acrylate or allyl methacrylate with a hydrosilane compound, with the use of a platinum-containing compound as catalyst, and an organic phosphorus compound as promoter selected from the group consisting of triphenylphosphine and an organic phosphorus compound expressed by Formula (III), $R^7R^8P(X)_mPR^9R^{10}$ (Formula III)

wherein $R^7$, $R^8$, $R^9$ and $R^{10}$ represent an alkyl group of carbon number 1–10 or an aryl group of carbon number 6–10, X represents $CH_2$ and m is 1, 2, 3 or 4.

2. A process according to claim 5, which comprises mixing the allyl acrylate or allyl methacrylate and the organic phosphorus compound followed by adding the platinum-containing compound, and then dropwise adding the hydrosilane compound.

* * * * *